(12) United States Patent
Bender et al.

(10) Patent No.: US 9,472,771 B2
(45) Date of Patent: Oct. 18, 2016

(54) METHOD OF MAKING AXIALLY FLUORINATED-PHTHALOCYANINES WITH AN APROTIC FLUORIDE COMPOUND

(71) Applicant: SABIC Global Technologies B.V., Amsterdam (NL)

(72) Inventors: Timothy P. Bender, Toronto (CA); Benoît H. Lessard, Toronto (CA); Trevor M. Grant, Toronto (CA)

(73) Assignee: SABIC Global Technologies B.V., Amsterdam (NL)

( * ) Notice: Subject to any disclaimer, the term of this patent is extended or adjusted under 35 U.S.C. 154(b) by 0 days.

(21) Appl. No.: 14/525,828

(22) Filed: Oct. 28, 2014

(65) Prior Publication Data

US 2015/0118788 A1    Apr. 30, 2015

Related U.S. Application Data

(60) Provisional application No. 61/898,226, filed on Oct. 31, 2013.

(51) Int. Cl.

| | |
|---|---|
| *H01L 21/00* | (2006.01) |
| *H01L 51/00* | (2006.01) |
| *C07F 7/02* | (2006.01) |
| *C07F 5/06* | (2006.01) |
| *C07F 5/00* | (2006.01) |
| *C07F 7/30* | (2006.01) |
| *C09B 47/08* | (2006.01) |
| *H01L 51/42* | (2006.01) |

(52) U.S. Cl.
CPC ........... *H01L 51/0078* (2013.01); *C07F 5/003* (2013.01); *C07F 5/069* (2013.01); *C07F 7/025* (2013.01); *C07F 7/30* (2013.01); *C09B 47/08* (2013.01); *H01L 51/0008* (2013.01); *H01L 51/0046* (2013.01); *H01L 51/4246* (2013.01); *Y02E 10/549* (2013.01)

(58) Field of Classification Search
CPC .......... H01L 51/00; H01L 51/42; C07F 5/00; C07F 7/30; C07F 7/02; C07F 5/06
USPC ....................... 438/382; 548/406; 252/519.21
See application file for complete search history.

(56) References Cited

U.S. PATENT DOCUMENTS

| | | | | |
|---|---|---|---|---|
| 2,227,628 | A | 1/1941 | Calcott et al. | ................ 362/284 |
| 3,281,426 | A * | 10/1966 | Van Dyke | .................... 540/140 |

(Continued)

FOREIGN PATENT DOCUMENTS

| | | |
|---|---|---|
| GB | 995186 | 6/1965 |
| GB | 2243917 | 11/1991 |
| WO | 2006/065038 | 6/2006 |

OTHER PUBLICATIONS

Database WPI Week 200878 Thomson Scientific, London, GB; AN 2008-N25751 XP002735829,—& CN 101255 163 (Chuangchun Appl Chem Res Inst Chinese Ac) Sep. 3, 2008 (Sep. 3, 2008) abstract p. 10 p. 11, line 7-line 14 example 8.

(Continued)

*Primary Examiner* — Caleb Henry
(74) *Attorney, Agent, or Firm* — Norton Rose Fulbright US LLP

(57) ABSTRACT

Disclosed is a method of making axially fluorinated metal phthalocyanines and their use in photovoltaic applications.

25 Claims, 4 Drawing Sheets

(56) References Cited

U.S. PATENT DOCUMENTS

| | | | |
|---|---|---|---|
| 4,209,458 A * | 6/1980 | Keller et al. | 558/420 |
| 4,304,719 A | 12/1981 | Wynne et al. | 260/314.5 |
| 4,315,093 A * | 2/1982 | Keller et al. | 528/362 |
| 4,351,776 A * | 9/1982 | Keller et al. | 558/419 |
| 5,656,751 A | 8/1997 | Tanaka et al. | 540/128 |
| 5,773,181 A * | 6/1998 | Molaire et al. | 430/78 |
| 5,788,914 A * | 8/1998 | Oi et al. | 252/587 |
| 6,511,971 B1 * | 1/2003 | Gorun | 514/183 |
| 6,514,651 B1 * | 2/2003 | Hayata | 430/56 |
| 6,896,945 B2 | 5/2005 | Berneth et al. | 428/64.1 |
| 7,585,363 B1 * | 9/2009 | Royster et al. | 106/412 |
| 7,628,849 B1 * | 12/2009 | Diehl et al. | 106/410 |
| 8,404,844 B2 * | 3/2013 | Kastler et al. | 546/37 |
| 9,080,055 B2 * | 7/2015 | Braun et al. | |
| 2004/0131958 A1 * | 7/2004 | Feng et al. | 430/32 |
| 2006/0211272 A1 | 9/2006 | Lee et al. | 438/789 |
| 2006/0234060 A1 * | 10/2006 | Gorun | 428/411.1 |
| 2007/0035497 A1 * | 2/2007 | Chen et al. | 345/87 |
| 2007/0041909 A1 * | 2/2007 | Kupussamy et al. | 424/9.362 |
| 2007/0215377 A1 * | 9/2007 | Aoki | 174/250 |
| 2008/0021173 A1 * | 1/2008 | Nakanishi et al. | 525/390 |
| 2008/0213620 A1 * | 9/2008 | Kim et al. | 428/690 |
| 2008/0268357 A1 * | 10/2008 | Wada et al. | 430/66 |
| 2009/0166614 A1 * | 7/2009 | Konemann et al. | 257/40 |
| 2010/0040966 A1 * | 2/2010 | Gu et al. | 430/37 |
| 2010/0207114 A1 * | 8/2010 | Koenemann | B82Y 10/00 257/40 |
| 2010/0233845 A1 * | 9/2010 | Gorun et al. | 438/99 |
| 2011/0095273 A1 * | 4/2011 | Meng et al. | 257/40 |
| 2011/0172437 A1 * | 7/2011 | Gorun et al. | 548/402 |
| 2011/0217544 A1 * | 9/2011 | Young et al. | 428/327 |
| 2011/0294054 A1 * | 12/2011 | Wu et al. | 430/58.75 |
| 2012/0052426 A1 * | 3/2012 | Qi et al. | 430/58.5 |
| 2012/0068123 A1 * | 3/2012 | Sundarraj et al. | 252/506 |
| 2012/0208989 A1 * | 8/2012 | Sun | 534/15 |
| 2012/0283430 A1 * | 11/2012 | Gorun et al. | 540/137 |
| 2012/0313087 A1 * | 12/2012 | Buchholz et al. | 257/40 |
| 2013/0064712 A1 * | 3/2013 | Roder et al. | 422/29 |
| 2013/0137025 A1 * | 5/2013 | Kawahara et al. | 430/56 |
| 2013/0291930 A1 * | 11/2013 | Braun et al. | 136/252 |
| 2014/0063590 A1 * | 3/2014 | Myoung et al. | 359/296 |
| 2014/0103635 A1 * | 4/2014 | Lehmann et al. | 283/85 |
| 2014/0227184 A1 * | 8/2014 | Groves et al. | 424/1.89 |
| 2014/0364630 A1 * | 12/2014 | Seeberger et al. | 549/348 |
| 2015/0031768 A1 * | 1/2015 | Groves et al. | 514/570 |
| 2015/0071862 A1 * | 3/2015 | Sabatino et al. | 424/9.61 |

OTHER PUBLICATIONS

Mark Schormann: "Neue Methoden zur Fluorierung von Verbindungenfrüher Übergangsmetalle", Dissertation, 2000, XP002735831, Retrieved from the Internet: URL:https://ediss.uni-goettingen.de/bitstream/handle/11858/00-1735-0000-0006-AE91-D/diss.pdf?sequence=1 [retrieved on Feb. 10, 2015] p. 28, paragraph 2.3.2.

Database WPI Week 201282 Thomson Scientific, London, GB; AN 2012-Q56826 XP002735828,—& JP 2012 232965 A (Dokuritsu Gyosei Hojin Busshitsu Zairyo) Nov. 29, 2012 (Nov. 29, 2012) abstract paragraph [0042] p. 34 paragraph [0215] figures 13,20 claim 12.

Database WPI Week 200010 Thomson Scientific, London, GB; AN 2000-111661 XP002735830,—& JP H11 349588 A (Mitsubishi Chem Corp) Dec. 21, 1999 (Dec. 21, 1999) abstract p. 6; example 7.

International Search Report issued in PCT/IB2014/065674 on Mar. 3, 2015.

* cited by examiner

METHOD OF MAKING AXIALLY FLUORINATED-PHTHALOCYANINES WITH AN APROTIC FLUORIDE COMPOUND

CROSS REFERENCE TO RELATED APPLICATIONS

This application claims the benefit of U.S. Provisional Application No. 61/898,226 filed Oct. 31, 2013. The contents of the referenced application are incorporated into the present application by reference.

BACKGROUND OF THE INVENTION

A. Field of the Invention

The invention generally concerns a process for making axially fluorinated-phthalocyanines and their use in photovoltaic applications.

B. Description of Related Art

Hydrogen fluoride (HF) gas and hydrofluoric acid are the primary industrial sources of fluorine or fluoride for a wide range of applications, including the production of fluorinated phthalocyanines (see U.S. Pat. No. 2,227,628). The reason for this is the highly acidic nature of these compounds, which allows for a more efficient chemical reaction to occur. A downside to their use, however, is that they are highly corrosive, which presents significant corrosion challenges to the equipment used in such production processes. To complicate matters, HF is lighter than air and can easily diffuse through porous substances. Further, both HF and hydrochloric acid are highly caustic to human tissue and both acute and chronically toxic, which also complicates the current production processes.

While attempts have been made to use other acids, these attempts also suffer from similar problems—acids in general are caustic in nature. Even further, and due in large part to fluorine's high electronegativity property, HF and hydrofluoric acid is produced as a by-product in such reactions, thereby presenting similar challenges to those mentioned above.

SUMMARY OF THE INVENTION

The present invention offers a solution to the aforementioned problems associated with HF gas and hydrofluoric acid. The solution resides in using an aprotic fluoride source as the fluorine donating source rather than HF or hydrofluoric acid. Further, the use of materials such as aprotic solvents avoids or limits the existence or production of free protons (H$^+$) during the chemical reaction process for making axially fluorinated-phthalocyanines. By limiting or preventing the presence of free protons (H$^+$) during the reaction, HF or hydrofluoric acid production as a by-product can be limited or avoided all together. Stated plainly, the solution offered by the present invention is a more efficient, cleaner, and safer process for making axially fluorinated-phthalocyanines when compared with those processes currently known in the art.

In one aspect of the present invention, there is disclosed a method of making an axially fluorinated metal phthalocyanine, the method comprising obtaining a composition comprising an aprotic fluoride compound, a solvent, and a compound having the following structure X$_m$Y$_n$-MPc and heating the composition for a sufficient period of time to produce an axially fluorinated metal phthalocyanine. Said produced axially fluorinated metal phthalocyanine compound can have the following structure F$_m$Y$_n$-MPc. The X and Y variables can each individually be Cl, Br, I, or —OH, m can be an integer of 1 or 2, n can be an integer of 0 or 1, M can be a trivalent or tetravalent metal, and Pc can be a phthalocyanine. Examples of trivalent metals include group III metals such as Al, Ga, or In. Examples of tetravalent metals include group IV metals such as Si, Ge, or Sn. In particular aspect, the starting phthalocyanine compound can be a mono- or bi-axially fluorinated metal Pc having the following structure:

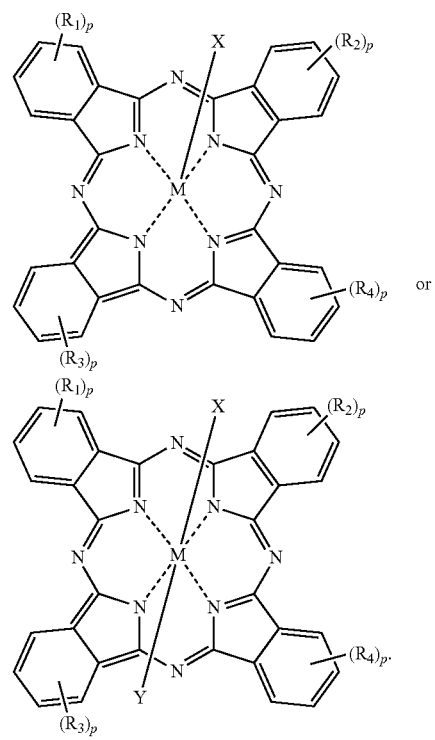

R$_1$, R$_2$, R$_3$, and R$_4$ can each individually be a hydrogen, a hydrocarbon, or a halogen, or a group in which a dissociable proton (H$^+$) is not present under a given set of reaction conditions and p can be an integer of 0 to 4. Examples of hydrocarbons or groups in which a dissociable proton (H$^+$) is not present include substituted or un-substituted hydrocarbons such as methyl, ethyl, propyl, isopropyl, n-butyl, sec-butyl or tert-butyl groups. Examples of halogens include fluorine, chlorine, bromine, or iodine. In certain aspects, the aprotic fluoride source that is used to donate a fluorine to the Pc can be a compound having the following general structure Z(F)$_o$, where Z is a group I or II metal, a tetra alkylated ammonium ion, or a tetra alkylated phosphonium ion, and o is 1 or 2. Examples of group I metals include Cs, Rb, K, Na, or Li, or more preferably Cs, Rb, or K. Examples of group II metals include Ba, Sr, Ca, Mg, or Be, or more preferably Ba, Sr, or Ca. In particular instances, and with reference to the above formulas, X is Cl, m is 1 or 2, and n is 0. In still further aspects, the composition can further include a chelating agent capable of chelating any free group I or group II metals or free tetra alkylated ammonium and phosphonium ions during the reaction process or any additional metals or compounds that could aid in the formation of free protons (H$^+$). Non-limiting examples of chelating agents include glycol, glycol mono ether, glycol bis ether, polyethylene glycol, polyethylene glycol mono ether, polyethylene glycol bis ether or a crown ether, or any combination thereof. Non-limiting examples of crown ethers include 18-crown-6 or dicyclohexyl-18-crown-6, dibenzo-18-crown-6, 15-crown-5, 12-crown-4, benzo-15-crown-5, benzo-18-crown-6,4'-aminobenzo-18-crown-6,4'-nitrobenzo-15-crown-5, or the like, or any combination thereof. The aprotic fluoride source and the starting Pc compound (e.g., $X_m Y_n$-MPc) can each be partially or fully solubilized in the composition. Similarly, the chelating agent can be partially or fully solubilized in the composition. The solvent used in the reaction composition can be an aprotic solvent such as a polar aprotic solvent. Examples of such polar aprotic solvents include dichloromethane (DCM), tetrahydrofuran (THF), ethyl acetate, propyl acetate, butyl acetate, isobutylacetate (and the like), acetone, dimethylformamide (DMF), acetonitrile (MeCN), benzonitrile, nitromethane, dimethyl sulfoxide (DMSO), propylene carbonate, or N-methyl-2-pyrrolidone (NMP), sulfolane (tetramethylene sulfone, 2,3,4,5-tetrahydrothiophene-1,1-dioxide), hexamethylphosphoramide (HMPA), methyl ethyl ketone, methyl isobutyl ketone, acetophenone, benzophenone, or the like, or any combination thereof. The reaction conditions can be such that the starting composition is heated to a temperature of 30 to 250° C. for 1 to 600 minutes. In particular aspects, the temperature range is 30 to 200° C., 30 to 175° C., 30 to 150° C., 30 to 125° C., 30 to 100° C., or 30 to 70° C. The time range can be 1 to 500, 1 to 400, 1 to 300, 1 to 200, 1 to 100, 1 to 50, or 1 to 25 minutes. Further, the starting composition can include 0.5 to 45% wt. of aprotic fluoride compound, and 0.1 to 50% wt. of the compound having the structure $X_m Y_n$-MPc. The amount can vary as needed (0.5 to 30, 0.5 to 20, 0.5 to 10, or 0.5 to 5 wt. % of an aprotic fluoride compound and 0.1 to 40, 0.1 to 30, 0.1 to 20, 0.1 to 10, or 0.1 to 5 wt. % of the compound having the structure $X_m Y_n$-MPc). The produced compound can be further purified or isolated by techniques known to those of skill in the art (e.g., filtration, precipitation, steam distillation, distillation evaporation, sublimation, centrifugation, decantation, or the like). The purified or isolated compound can be in a dry or powdered form or can be stored within a liquid. The produced compound can be further modified with a dopant so as to enhance its p-type or n-type properties. The produced compounds can be semi-conductive compounds and can be used in such semi-conductor applications. In certain aspects, the starting composition does not include a protic compound or does not include a protic fluoride compound or both. (e.g., HF and hydrofluoric acid are not included in the starting composition as a source for fluorine donation). Further, the reaction process does not produce or produces only trace or minimal amounts of hydrogen fluoride as a by-product when compared with other processes. In particular embodiments, the resulting or produced axially fluorinated metal phthalocyanine can have the following structure:

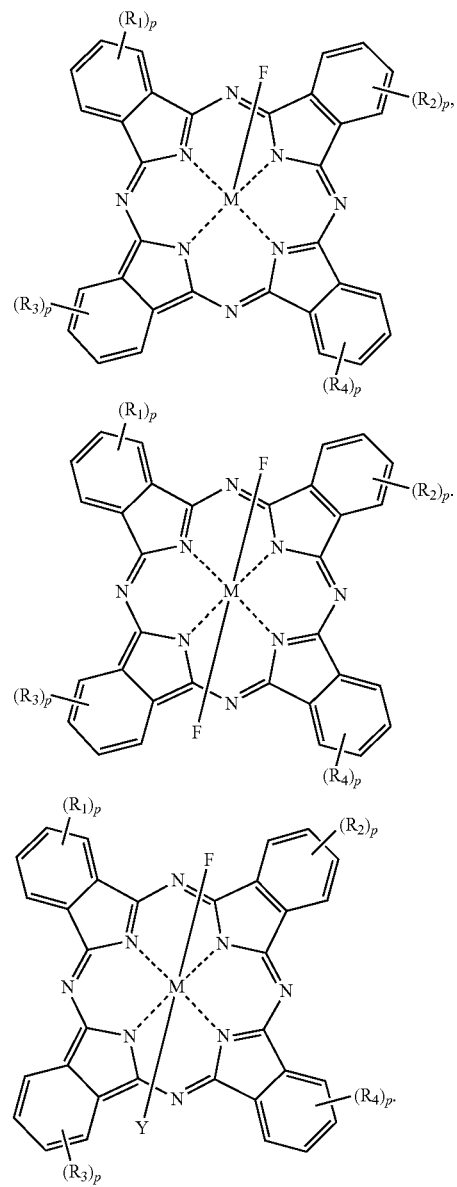

In still another embodiment of the present invention, there is disclosed a composition comprising an aprotic fluoride compound, a solvent, and a compound having the following structure $X_m Y_n$-MPc, with the X, Y, m, n, M, and Pc variables disclosed above. Similarly, the aprotic fluoride compound can have the following structure $Z(F)_o$, with the Z and o variables disclosed above. This composition can be the starting composition or reaction mixture used to produce the axially fluorinated-phthalocyanines. Each of the ingredients in the composition can be partially or fully solubilized or suspended in said composition. This starting composition or reaction mixture can be free of protic compounds or acids that have labile protons ($H^+$). Examples of such compounds include protic solvents, HF gas, and hydrofluoric acid.

In another embodiment of the present invention, it was discovered that axially fluorinated metal phthalocyanines (e.g., mono- and bi-axially fluorinated metal Pcs) can be used in photovoltaic applications. The fluorinated metal phthalocyanines can be those produced by the processes of the present invention or those produced by known processes.

These axially fluorinated metal phthalocyanines can be used in an active layer of a photovoltaic cell. The photovoltaic cell can include a transparent substrate, a transparent electrode, the photoactive layer, and a second electrode, wherein the photoactive layer is disposed between the transparent electrode and the second electrode. The transparent electrode can be a cathode and the second electrode can be an anode. Alternatively, the transparent electrode can be an anode and the second electrode can be a cathode. The second electrode can or may not be transparent. Due to the nature of the axially fluorinated metal phthalocyanines, the photovoltaic cell does not have to include an electrolyte. The photovoltaic cell can be designed such that it is a single active layer, bi-layer, or a tri-layer photovoltaic cell. In a bi-layer photovoltaic cell, one layer can be an axially fluorinated metal phthalocyanines and another layer can be a different metal phthalocyanines. A bulk-heterojunction layer can be produced by mixing the axially fluorinated metal phthalocyanines with polymers. The photovoltaic cell can be included in an organic electronic device. Examples of such devices include polymeric organic light-emitting diode (PLED), an organic integrated circuit (O-IC), an organic field effect transistor (OFET), an organic thin film transistor (OTFT), an organic solar cell (O-SC) or an organic laser diode (O-laser). In certain instances, and in view of the processes of the present invention, the photoactive layer may not include hydrogen fluoride or hydrofluoric acid. The photoactive layer can be deposited on at least a portion of a surface of a substrate or electrode(s). Examples of such deposition processes include vacuum deposition or organic phase vapor deposition.

Also disclosed are embodiments 1 to 62. Embodiment 1 is a method of making an axially fluorinated metal phthalocyanine, the method comprising: (a) obtaining a composition comprising an aprotic fluoride compound, a solvent, and a compound having the following structure: $X_mY_n$-MPc; and (b) heating the composition for a sufficient period of time to produce an axially fluorinated metal phthalocyanine having the following structure: $F_mY_n$-MPc, where X and Y are each individually Cl, Br, I, or —OH, m is 1 or 2, n is 0 or 1, M is a trivalent or tetravalent metal, and Pc is a phthalocyanine. Embodiment 2 is the method of embodiment 1, wherein the aprotic fluoride compound has the following structure: $Z(F)_o$, wherein Z is a group I or II metal, a tetra alkylated ammonium ion, or a tetra alkylated phosphonium ion, and o is 1 or 2. Embodiment 3 is the method of embodiment 2, wherein Z is a group I metal selected from Cs, Rb, K, Na, or Li, or more preferably Cs, Rb, or K. Embodiment 4 is the method of embodiment 2, wherein Z is a group II metal selected from Ba, Sr, Ca, Mg, or Be, or more preferably Ba, Sr, or Ca. Embodiment 5 is the method of any one of embodiments 1 to 4, wherein X is Cl, m is 1 or 2, and n is 0. Embodiment 6 is the method of any one of embodiments 1 to 4, wherein m is 1 and n is 1. Embodiment 7 is the method of any one of embodiments 1 to 6, wherein M is a group III metal selected from the group consisting of Al, Ga, or In. Embodiment 8 is the method of any one of embodiments 1 to 6, wherein M is a group IV metal selected from the group consisting of Si, Ge, or Sn. Embodiment 9 is the method of any one of embodiments 1 to 8, wherein the produced axially fluorinated metal phthalocyanine has the following structure:

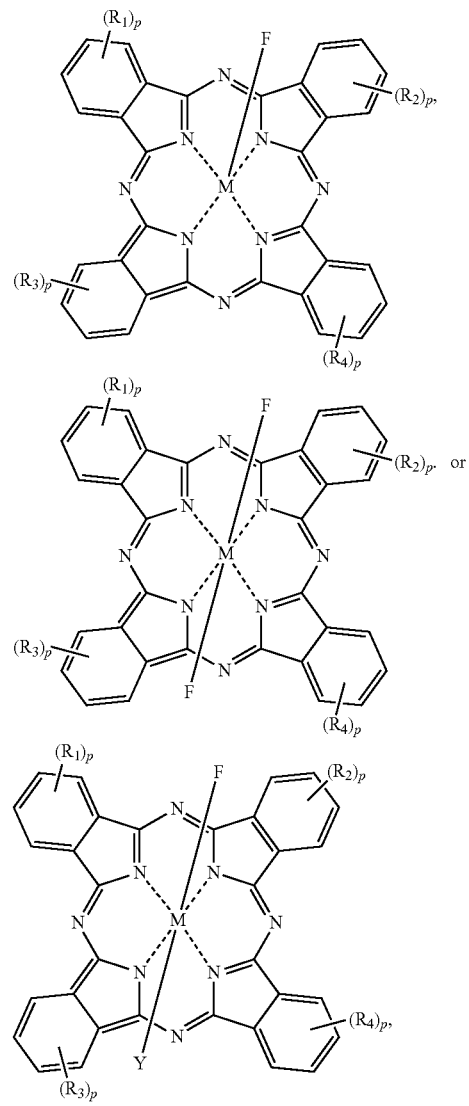

where $R_1$, $R_2$, $R_3$, and $R_4$ are each individually a hydrogen, a hydrocarbon, or a halogen, and p is an integer from 0 and 4. Embodiment 10 is the method of embodiment 9, wherein $R_1$ to $R_4$ are each individually a substituted or un-substituted hydrocarbon. Embodiment 11 is the method of embodiment 10, wherein the hydrocarbon is a methyl, ethyl, propyl, isopropyl, n-butyl, sec-butyl or tert-butyl group. Embodiment 12 is the method of embodiment 9, wherein $R_1$ to $R_4$ are each individually a halogen selected from F, Cl, Br, or I. Embodiment 13 is the method of any one of embodiments 1 to 12, wherein the composition further comprises a chelating agent. Embodiment 14 is the method of embodiment 13, wherein the chelating agent is a glycol, glycol mono ether, glycol bis ether, polyethylene glycol, polyethylene glycol mono ether, polyethylene glycol bis ether or a crown ether. Embodiment 15 is the method of embodiment 14, wherein the crown ether is 18-crown-6 or dicyclohexyl-18-crown-6, dibenzo-18-crown-6, 15-crown-5, 12-crown-4, benzo-15-crown-5, benzo-18-crown-6,4'-aminobenzo-18-crown-6,4'-nitrobenzo-15-crown-5 or the like. Embodiment 16 is the method of any one of embodiments 1 to 15, wherein the aprotic fluoride compound and the compound having the structure $X_mY_n$-MPc are each partially or fully solubilized in the composition. Embodiment 17 is the method of embodiment 16, wherein the chelating agent is partially or fully solubilized in the composition. Embodiment 18 is the method of any one of embodiments 1 to 17, wherein the solvent is an aprotic solvent. Embodiment 19 is the method of embodiment 18, wherein the polar aprotic solvent is dichloromethane (DCM), tetrahydrofuran (THF), ethyl acetate, propyl acetate, butyl acetate, isobutylacetate (and the like), acetone, dimethylformamide (DMF), acetonitrile (MeCN), benzonitrile, nitromethane, dimethyl sulfoxide (DMSO), propylene carbonate, or N-methyl-2-pyrrolidone (NMP), sulfolane (tetramethylene sulfone, 2,3,4,5-tetrahydrothiophene-1,1-dioxide), hexamethylphosphoramide (HMPA), methyl ethyl ketone, methyl isobutyl ketone, acetophenone, benzophenone, or the like, or any combination thereof. Embodiment 20 is the method of any one of embodiments 1 to 19, wherein the composition is heated to a temperature of 30 to 250° C. for 1 to 600 minutes. Embodiment 21 is the method of any one of embodiments 1 to 20, wherein the composition in step (a) comprises 0.5 to 45% wt. of aprotic fluoride compound, and 0.1 to 50% wt. of the compound having the structure $X_mY_n$-MPc. Embodiment 22 is the method of any one of embodiments 1 to 21, further comprising purifying or isolating the produced compound. Embodiment 23 is the method of embodiment 22, wherein the compound is purified or isolated by filtration, precipitation, steam distillation, distillation evaporation, sublimation, centrifugation, decantation, or the like. Embodiment 24 is the method of embodiment 23, wherein the purified or isolated compound is in dry or powdered form. Embodiment 25 is the method of any one of embodiments 1 to 24, wherein the produced compound is modified with a dopant so as to enhance its p-type or n-type properties. Embodiment 26 is the method of any one of embodiments 1 to 25, wherein the produced axially fluorinated metal phthalocyanine is a semi-conductor. Embodiment 27 is the method of any one of embodiments 1 to 26, wherein the composition in step (a) does not include a protic compound or does not include a protic fluoride compound or does not include an acid. Embodiment 28 is the method of embodiment 27, wherein the protic fluoride compound is hydrogen fluoride. Embodiment 29 is the method of any one of embodiments 1 to 28, wherein the method does not produce hydrogen fluoride or hydrofluoric acid as a by-product or produces only trace amounts of said hydrogen fluoride or hydrochloric acid. Embodiment 30 is a photovoltaic cell comprising a photoactive layer comprising an axially fluorinated metal phthalocyanine. Embodiment 31 is the photovoltaic cell of embodiment 30, wherein the axially fluorinated metal phthalocyanine is produced by the process of any one of embodiments 1 to 29. Embodiment 32 is the photovoltaic cell of any one of embodiments 30 to 31, comprising a transparent substrate, a transparent electrode, the photoactive layer, and a second electrode, wherein the photoactive layer is disposed between the transparent electrode and the second electrode. Embodiment 33 is the photovoltaic cell of embodiment 32, wherein the transparent electrode is a cathode and the second electrode is an anode. Embodiment 34 is the photovoltaic cell of embodiment 32, wherein the transparent electrode is an anode and the second electrode is a cathode. Embodiment 35 is the photovoltaic cell of any one embodiments 30 to 34, wherein the second electrode is not transparent. Embodiment 36 is the photovoltaic cell of any one of embodiments 30 to 35, wherein photovoltaic cell does not include an electrolyte. Embodiment 37 is the photovoltaic cell of any one of embodiments 30 to 36, wherein photovoltaic cell is a bi-layer photovoltaic cell or a tri-layer photovoltaic cell. Embodiment 38 is the photovoltaic cell of embodiment 37, wherein the first layer of the bi-layer is an axially fluorinated metal phthalocyanines and the second layer of the bi-layer is different metal phthalocyanines. Embodiment 39 is the photovoltaic cell of any one of embodiments 30 to 38, wherein the photovoltaic cell is comprised in an organic electronic device. Embodiment 40 is the photovoltaic cell of embodiment 39, wherein the organic electronic device is a polymeric organic light-emitting diode (PLED), an organic integrated circuit (O-IC), an organic field effect transistor (OFET), an organic thin film transistor (OTFT), an organic solar cell (O-SC) or an organic laser diode (O-laser). Embodiment 41 is the photovoltaic cell of any one of embodiments 30 to 40, wherein the photoactive layer comprising the axially fluorinated metal phthalocyanine does not include hydrogen fluoride. Embodiment 42 is a process for making a photoactive layer on a substrate, wherein the photoactive layer comprises an axially fluorinated metal phthalocyanine, the process comprising depositing the axially fluorinated metal phthalocyanine on at least a portion of a surface of the substrate. Embodiment 43 is the process of embodiment 42, wherein the axially fluorinated metal phthalocyanine is deposited by vacuum deposition or organic phase vapor deposition. Embodiment 44 is the process of embodiment 41 or 43, wherein the axially fluorinated metal phthalocyanine is produced by the process of any one of embodiments 1 to 29. Embodiment 45 is a composition comprising: (a) an aprotic fluoride compound; (b) a solvent; and (c) a compound having the following structure: $X_mY_n$-MPc; and where X and Y are each individually Cl, Br, I, or —OH, m is 1 or 2, n is 0 or 1, M is a trivalent or tetravalent metal, and Pc is a phthalocyanine. Embodiment 46 is the composition of embodiment 45, wherein the aprotic fluoride compound has the following structure: $Z(F)_o$, wherein Z is a group I or II metal, a tetra alkylated ammonium ion, or a tetra alkylated phosphonium ion, and o is 1 or 2. Embodiment 47 is the composition of embodiment 46, wherein Z is a group I metal selected from Cs, Rb, K, Na, or Li, or more preferably Cs, Rb, or K. Embodiment 48 is the composition of embodiment 46, wherein Z is a group II metal selected from Ba, Sr, Ca, Mg, or Be, or more preferably Ba, Sr, or Ca. Embodiment 49 is the composition of any one of embodiments 45 to 48, wherein X is Cl, m is 1 or 2, and n is 0. Embodiment 50 is the composition of any one of embodiments 45 to 48, wherein m is 1 and n is 1. Embodiment 51 is the composition of any one of embodiments 45 to 50, wherein M is a group III metal selected from the group consisting of Al, Ga, In, and any combination thereof. Embodiment 52 is the composition of any one of embodiments 45 to 50, wherein M is a group IV metal selected from the group consisting of Si, Ge, Sn, and any combination thereof. Embodiment 53 is the composition of any one of embodiments 45 to 52, wherein the composition further comprises a chelating agent. Embodiment 54 is the composition of embodiment 53, wherein the chelating agent is a glycol, glycol mono ether, glycol bis ether, polyethylene glycol, polyethylene glycol mono ether, polyethylene glycol bis ether or a crown ether. Embodiment 55 is the composition of embodiment 54, wherein the crown ether is 18-crown-6 or dicyclohexyl-18-crown-6, dibenzo-18-crown-6, 15-crown-5, 12-crown-4, benzo-15-crown-5, benzo-18-crown-6,4'-aminobenzo-18-crown-6,4'-nitrobenzo-15-crown-5, or the like. Embodiment 56 is the composition of any one of embodiments 45 to 55, wherein the aprotic fluoride compound and the compound having the structure $X_mY_n$-MPc are each partially or fully solubilized in the composition. Embodiment 57 is the composition of embodiment 56, wherein the chelating agent is partially or fully solubilized in the composition. Embodiment 57 is the composition of any one of embodiments 45 to 57, wherein the solvent is a polar aprotic solvent. Embodiment 59 is the composition of embodiment 58, wherein the polar aprotic solvent is dichloromethane (DCM), tetrahydrofuran (THF), ethyl acetate, propyl acetate, butyl acetate, isobutylacetate (and the like), acetone, dimethylformamide (DMF), acetonitrile (MeCN), benzonitrile, nitromethane, dimethyl sulfoxide (DMSO), propylene carbonate, or N-methyl-2-pyrrolidone (NMP), sulfolane (tetramethylene sulfone, 2,3,4,5-tetrahydrothiophene-1,1-dioxide), hexamethylphosphoramide (HMPA), methyl ethyl ketone, methyl isobutyl ketone, acetophenone, benzophenone, or the like, or any thereof. Embodiment 60 is the composition of any one of embodiments 45 to 59, wherein the composition in step (a) comprises 0.5 to 45% wt. of aprotic fluoride compound, and 0.1 to 50% wt. of the compound having the structure $X_mY_n$-MPc. Embodiment 61 is the composition of any one of embodiments 45 to 60, wherein the composition does not include a protic compound or does not include a protic fluoride compound or both. Embodiment 62 is the composition of embodiment 61, wherein the protic fluoride compound is hydrogen fluoride.

The term "aprotic" when used in the context of "aprotic fluoride sources" or "aprotic fluoride compounds" or "aprotic compounds" or "aprotic solvents" means that the sources, compounds, and solvents are such that they do not include a dissociable hydrogen such that a significant amount of free protons ($H^+$) are or become present during the reaction process (e.g., they have no H groups having a pKa less than 10 or alternatively, no less than 15, or alternatively no less than 20, or alternatively no less than 30).

The phrases "trace amount" or "minimal amount" in the context of HF or hydrofluoric acid production in the context of the present invention includes amounts of less than 1 part per thousand (ppt) or 1 part per million (ppm) during or after the reaction process has been completed.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The processes of making the axially fluorinated metal phthalocyanines, the starting compositions or reaction mixtures, the photoactive layers, the photovoltaic cells, and the organic electronic devices of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the aforesaid processes, compositions, photoactive layers, and photovoltaic cells of the present invention are their non-use of HF or hydrofluoric acid to produce the axially fluorinated metal phthalocyanines as well as the lack of HF or hydrofluoric acid production as a by-product during said reaction procedures.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Figure 1:
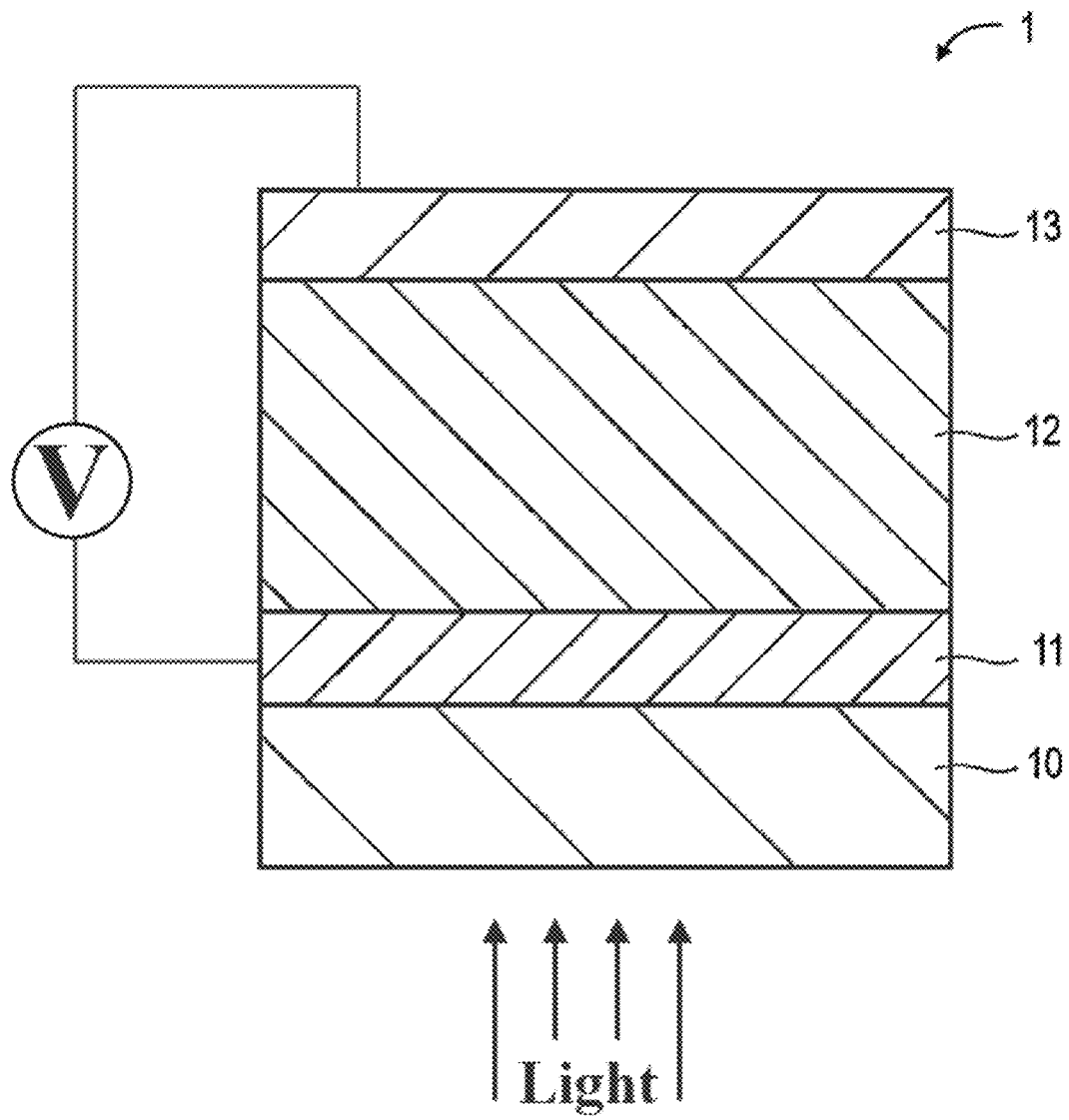
FIG. 1: Illustration of an organic photovoltaic cell incorporating the polymers of the present invention.

As noted above, the present invention offers a solution to the problems associated with the use or production of hydrogen fluoride (HF) and hydrofluoric acid in chemical reactions used to make axially fluorinated-phthalocyanines. In short, the solution resides in using an aprotic fluoride source as the fluorine donating source and limiting or preventing the presence of free protons ($H^+$) during the chemical reaction process. These and other non-limiting aspects of the present invention are provided in the following subsections.

A. Process for Making Axially Fluorinated-Phthalocyanines

The following reaction scheme illustrates a non-limiting embodiment of making mono-axially fluorinated-phthalocyanines present invention:

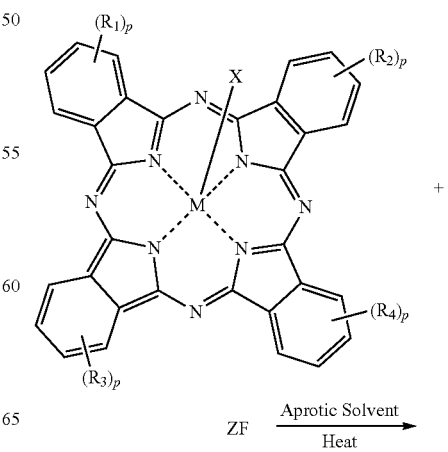

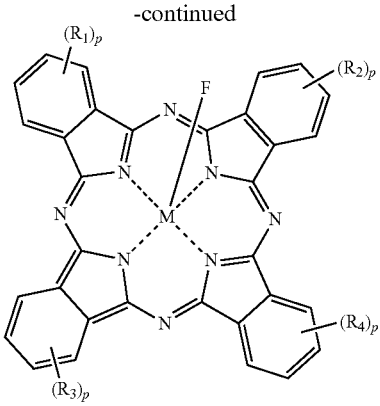

where X is Cl, Br, I, or —OH, M is a trivalent or tetravalent metal, $R_1$ to $R_4$ are each individually a hydrogen, a hydrocarbon, or a halogen, or a group in which a dissociable proton ($H^+$) is not present under a given set of reaction conditions, p is 0 to 4, and Z is a group I metal, a tetra alkylated ammonium ion, or a tetra alkylated phosphonium ion.

The following reaction schemes illustrates non-limiting embodiments of making bi-axially fluorinated-phthalocyanines present invention:

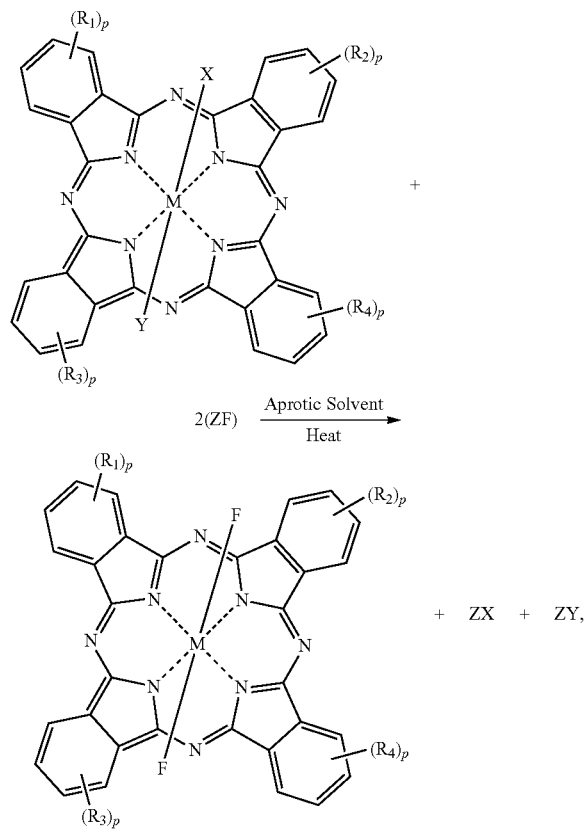

where X and Y are each individually Cl, Br, I, or —OH, M is a trivalent or tetravalent metal, $R_1$ to $R_4$ are each individually a hydrogen, a hydrocarbon, or a halogen, or a group in which a dissociable proton ($H^+$) is not present under a given set of reaction conditions, p is 0 to 4, and Z is a group I metal, a tetra alkylated ammonium ion, or a tetra alkylated phosphonium ion, or

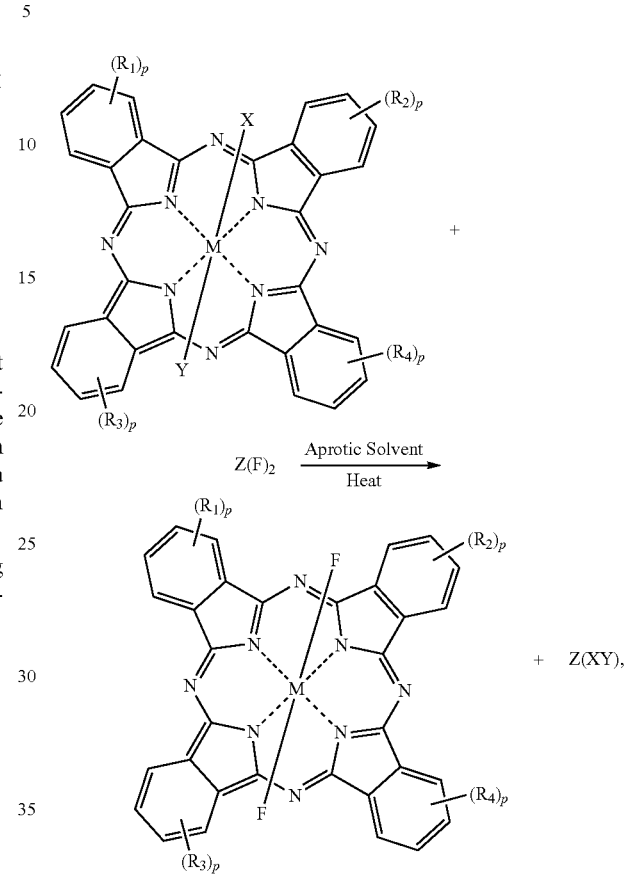

where X and Y are each individually Cl, Br, I, or —OH, M is a trivalent or tetravalent metal, $R_1$ to $R_4$ are each individually a hydrogen, a hydrocarbon, or a halogen, or a group in which a dissociable proton ($H^+$) is not present under a given set of reaction conditions, p is 0 to 4, and Z is a group II metal.

Notably, hydrogen fluoride and hydrofluoric acid is not utilized nor produced as a reaction by-product in any of these processes. Specific non-limiting examples of mono- and bi-axially fluorinated-phthalocyanines are provided in the Examples section of this application. Also, non-limiting examples of aprotic solvents, trivalent and tetravalent metals, group I and II metals, tetra alkylated ammonium ions, and tetra alkylated phosphonium ions are provided in other sections of this application and are incorporated into this section by reference.

In addition to the aprotic solvent, chelating agents can be included in the above reactions. Such agents can be useful in binding any potentially free metals, alkylated ammonium ions, or tetra alkylated phosphonium ions during the reaction procedure. This can further aid in preventing the formation of hydrogen fluoride during said reaction processes. The chelating agents should be such that they do not include dissociable protons under the given reaction conditions. Non-limiting examples of such chelating agents have been provided in other sections of this application and are incorporated into this section by reference.

Further, the reaction conditions can be such that the starting composition is heated to a temperature of 30 to 250° C. for 1 to 600 minutes. In particular aspects, the temperature range is 30 to 200° C., 30 to 175° C., 30 to 150° C., 30 to 125° C., 30 to 100° C., or 30 to 70° C. The time range can be 1 to 500, 1 to 400, 1 to 300, 1 to 200, 1 to 100, 1 to 50, or 1 to 25 minutes. Further, the starting composition can include 0.5 to 45% wt. of aprotic fluoride compound, and 0.1 to 50% wt. of the compound having the structure $X_mY_n$-MPc. The amount can vary as needed (0.5 to 30, 0.5 to 20, 0.5 to 10, or 0.5 to 5 wt. % of an aprotic fluoride compound and 0.1 to 40, 0.1 to 30, 0.1 to 20, 0.1 to 10, or 0.1 to 5 wt. % of the compound having the structure $X_mY_n$-MPc).

The starting materials used in the processes of the present invention are commercially available from common pigment and colorant suppliers or alternatively can also be easily prepared by known synthetic routes. For instance, the Cl—AlPc can be easily made by cyclotetramerization of phthalonitrile on reaction with $AlCl_3$ at elevated temperatures. Alternatively Cl—AlPc can be made by reaction of metal free phthalocyanine:

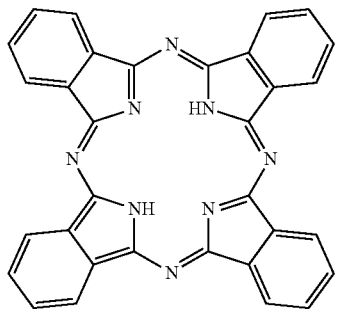 [SMILES: c1ccc2c(c1)-c1nc-2nc2[nH]c(nc3nc(nc4[nH]c(n1)c1ccccc41)-c1ccccc1-3)c1ccccc21]

with $AlCl_3$ in a so-called metal insertion reaction. Cl—GaPc can be similarly made but is preferably made by the cyclotetramerization of 1,3-diiminoisoindoline at elevated temperatures in the presence of $GaCl_3$. Similarly $Cl_2$—SiPc can be made by cyclotetramerization of 1,3-diiminoisoindoline at elevated temperatures in the presence of $SiCl_4$. $Cl_2$—GePc can be made by cyclotetramerization of phthalonitrile on reaction with $GeCl_4$ at elevated temperatures.

B. Organic Photovoltaic Cells

An additional discovery in the context of the present invention is the use of axially fluorinated-phthalocyanines in photovoltaic applications, such as organic photovoltaic cells. While the axially fluorinated-phthalocyanines made by the processes of the present invention can be used in photovoltaic applications, axially fluorinated-phthalocyanines produced by other processes can also be used in such applications. That is to say, the inventors have discovered that axially fluorinated-phthalocyanines are useful in photovoltaic applications irrespective of how said axially fluorinated-phthalocyanines are produced. Further, the use of these small molecules provide for a more efficient processing of photoactive layers when compared to photoactive polymeric layers.

FIG. 1 is a cross-sectional view of a non-limiting organic photovoltaic cell that axially fluorinated-phthalocyanines can be incorporated into. The organic photovoltaic cell (1) can include a transparent substrate (10), a front electrode (11), a photoactive layer (12), and a back electrode (13). Additional materials, layers, and coatings (not shown) known to those of ordinary skill in the art can be used with photovoltaic cell (1), some of which are described below.

Generally speaking, the organic photovoltaic cell (1) can convert light into usable energy by: (a) photon absorption to produce excitons; (b) exciton diffusion; (c) charge transfer; and (d) charge-transportation to the electrodes. With respect to (a), the excitons are produced by photon absorption by the photoactive layer (12), which can be a single layer such that the axially fluorinated-phthalocyanines are the active light absorbing component in the layer. Alternatively, the photoactive layer (12) can be a mixture of p-type and n-type organic semiconductor materials (e.g., bulk heterojunction) or can be separate p-type and n-type layers adjacent to one another (i.e., bi-layer heterojunction). In preferred aspects, the layer (12) is a single layer in which the active component comprises the axially fluorinated-phthalocyanines. For (b), the generated excitons diffuse to the p-n junction. Then in (c), the excitons separate into electrons and holes. For (d), electrons and holes are transported to the electrodes (11) and (13) and are used in a circuit.

1. Substrate (10)

The substrate (10) can be used as support. For organic photovoltaic cells, it is typically transparent or translucent, which allows light to efficiently enter the cell. It is typically made from material that is not easily altered or degraded by heat or organic solvents, and as already noted, has excellent optical transparency. Non-limiting examples of such materials include inorganic materials such as alkali-free glass and quartz glass, polymers such as polyethylene, PET, PEN, polyimide, polyamide, polyamidoimide, liquid crystal polymer, and cycloolefin polymer, silicon, and metal.

2. Front Electrode and Back Electrodes (11) and (13)

The front electrode (11) can be used as a cathode or anode depending on the set-up of the circuit. It is stacked on the substrate (10). The front electrode (11) can be made of a transparent or translucent conductive material. Typically, the front electrode (11) is obtained by forming a film using such a material (e.g., vacuum deposition, sputtering, ion-plating, plating, coating, etc.). Non-limiting examples of transparent or translucent conductive material include metal oxide films, metal films, and conductive polymers. Non-limiting examples of metal oxides that can be used to form a film include indium oxide, zinc oxide, tin oxide, and their complexes such as indium stannate (ITO), fluorine-doped tin oxide (FTO), and indium zinc oxide films. Non-limiting examples of metals that can be used to form a film include gold, platinum, silver, and copper. Non-limiting examples of conductive polymers include polyaniline and polythiophene. The thickness of the film for the front electrode (11) is typically between from 30 to 300 nm. If the film thickness is less than 30 nm, then the conductivity can be reduced and the resistance increased, which results in a decrease in photoelectric conversion efficiency. If the film thickness is greater than 300 nm, then light transmittance may be lowered. Also, the sheet resistance of the front electrode (11) is typically 10Ω/□ or less. Further, the front electrode (11) may be a single layer or laminated layers formed of materials each having a different work function.

The back electrode (13) can be used as a cathode or anode depending on the set-up of the circuit. This electrode (13) can be stacked on the photoactive layer (12). The material used for the back electrode (13) can be conductive. Non-limiting examples of such materials include metals, metal oxides, and conductive polymers (e.g., polyaniline, polythiophene, etc.) such as those discussed above in the context of the front electrode (11). When the front electrode (11) is formed using a material having high work function, then the back electrode (13) can be made of material having a low work function. Non-limiting examples of materials having a low work function include Li, In, Al, Ca, Mg, Sm, Tb, Yb, Zr, Na, K, Rb, Cs, Ba, and the alloys thereof. The back electrode (13) can be a single layer or laminated layers formed of materials each having a different work function. Further, it may be an alloy of one or more of the materials having a low work function and at least one selected from the group consisting of gold, silver, platinum, copper, manganese, titanium, cobalt, nickel, tungsten, and tin. Examples of the alloy include a lithium-aluminum alloy, a lithium-magnesium alloy, a lithium-indium alloy, a magnesium-silver alloy, a magnesium-indium alloy, a magnesium-aluminum alloy, an indium-silver alloy, and a calcium-aluminum alloy. The film thickness of the back electrode (13) can be from 1 to 1000 nm or from 10 to 500 nm. If the film thickness is too small, then the resistance can be excessively large and the generated charge may not be sufficiently transmitted to the external circuit.

In some embodiments, the front (11) and back (13) electrodes can be further coated with hole transport or electron transport layers (not shown in FIG. 1) to increase the efficiency and prevent short circuits of the organic photovoltaic cell (1). The hole transport layer and the electron transport layer can be interposed between the electrode and the photoactive layer (12). Non-limiting examples of the materials that can be used for the hole transport layer include polythiophene-based polymers such as PEDOT/PSS (poly(3,4-ethylenedioxythiophene)-poly(styrene sulfonate)) and organic conductive polymers such as polyaniline and polypyrrole. The film thickness of the hole transport layer can be from 20 to 100 nm. If the film thickness is too thin, short circuit of the electrode can occur more readily. If the film thickness is too thick, the film resistance is large and the generated electric current could be limited and optical conversion efficiency can be reduced. As for the electron transport layer, it can function by blocking holes and transporting electrons more efficiently. Non-limiting examples of the type of material that the electron transport layer can be made of include metal oxides (e.g., amorphous titanium oxide). When titanium oxide is used, the film thickness can range from 5 to 20 nm. If the film thickness is too thin, the hole blocking effect can be reduced and thus the generated excitons are deactivated before the excitons dissociate into electrons and holes. By comparison, when the film thickness is too thick, the film resistance is large, the generated electric current is limited, resulting in reduction of optical conversion efficiency.

3. Photoactive Layer (12)

The photoactive layer (12) can be interposed between the front electrode (10) and the back electrode (13). In one instance, the photoactive layer (12) can be a single layer such that the axially fluorinated-phthalocyanines (e.g., those produced by the processes of the present invention or by other process known in the art) are the active light absorbing component in the layer. Alternatively, the photoactive layer (12) can be a bulk hetero-junction type layer such that the axially fluorinated-phthalocyanines (e.g., those produced by the processes of the present invention or by other process known in the art) are mixed with a second semi-conductive material (e.g., a polymer or a small molecule) and a micro phase separation occurs within said layer (12). Further, the photoactive layer (12) can be a bi-layer hetero-junction type layer such that the axially fluorinated-phthalocyanines form one layer and another photoactive layer is adjacent thereto. In some embodiments, the bi-layer hetero-junction can be one type of axially fluorinated-phthalocyanine for one layer and a different metal phthalocyanines (for example, an axially chlorinated-phthalocyanine) for the other layer. In such a bi-layer, the thickness of axially fluorinated-phthalocyanine layer can be about 20 nm and the thickness of the other phthalocyanine can be about 40 nm. In one embodiment, the axially chlorinated-phthalocyanines can be an electron acceptor. In another embodiment the photoactive layer (12) can be a tri-layer. For example, a photoactive layer containing layers of axially fluorinated-phthalocyanines, chlorinated-phthalocyanines, and fullerene. In all instances, the layer (12) can absorb light and allow for the flow of electrons to and from the electrodes (11 and 13). Further, there can be multiple photoactive layers used for a given photovoltaic cell (e.g., 2, 3, 4, or more).

In instances, where the photoactive layer (12) is a layer of the axially fluorinated-phthalocyanines, the layer can be deposited on at least a portion of a surface of the electrodes (11 and 13) or on the substrate (10) or both by vacuum thermal evaporation, which involves the heating of an organic material in vacuum and depositing said material, or by organic vapor phase deposition, which involves evaporation of the organic material over a substrate in the presence of an inert carrier gas. In instances where the axially fluorinated-phthalocyanines are mixed with photoactive polymers, a solution can be prepared that includes a solvent, the polymers, and the axially fluorinated-phthalocyanines fully or partially solubilized therein. Non-limiting examples of such solvents include the polar aprotic solvents discussed above as well as any of the following solvents: unsaturated hydrocarbon-based solvents such as toluene, xylene, tetralin, decalin, mesitylene, n-butylbenzene, sec-butylbutylbenzene, and tert-butylbenzene; halogenated aromatic hydrocarbon-based solvents such as chlorobenzene, dichlorobenzene, and trichlorobenzene, halogenated saturated hydrocarbon-based solvents such as carbon tetrachloride, chloroform, dichloromethane, dichloroethane, chlorobutane, bromobutane, chloropentane, chlorohexane, bromohexane, and chlorocyclohexane, and ethers such as tetrahydrofuran and tetrahydropyran. The solution can be deposited by doctor blade coating, spin coating, meniscus coating, transfer printing, ink jet printing, offset printing, screen printing process, dip coating, casting, bar coating, roll coating, wire bar coating, spraying, screen printing, gravure printing, flexo printing, offset printing, gravure offset printing, dispenser coating, nozzle coating, capillary coating, etc.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of Difluorosiliconphthalocyanine ($F_2$—SiPc

In a 50 mL three neck round-bottom flask with a reflux condenser and nitrogen inlet, $Cl_2$—SiPc (0.1 g, 0.163 mmol) and cesium fluoride (0.06 g, 0.395 mmol) were dissolved in DMF (1 mL). The mixture was stirred and heated at 150° C. under nitrogen for 30 minutes. The crude product was allowed to cool to 130° C. and was precipitated into 150 mL of isopropanol. The final product was gravity filtered resulting in a fine dark indigo powder. The yield was 71% (0.068 g). The spectral and mass properties were measured and are: UV-vis (DMSO) $\lambda_{max}$=688 nm; high resolution mass spectrometry (HRMS) [M+] calculated 578.1231, found 578.1235. The produced molecule has the following structure:

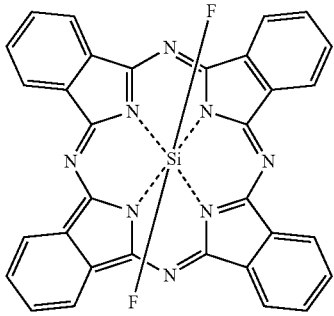

Example 2

Synthesis of Fluoroaluminumphthalocyanine (F—AlPc)

The synthesis of F—AlPc was performed under similar conditions to that of $F_2$—SiPc, except using Cl—AlPc as the starting material. The yield was 70-80% (0.70 g to 0.08 g) with a purity of greater than 99%. The spectral and mass properties were measured and are: UV-vis (DMSO) $\lambda_{max}$=671 nm; HRMS [M+] calculated 558.1324, found 554.1341. The produced molecule has the following structure:

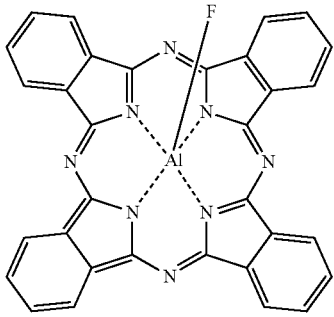

Example 3

Synthesis of Fluorogalliumphthalocyanine (F—GaPc)

The synthesis of F—GaPc was performed under similar conditions to that of $F_2$—SiPc, except using Cl—GaPc as the starting material, as well as the addition of a crown either. Cl—GaPc (0.1 g, 0.16 mmol), cesium fluoride (0.03 g, 0.2 mmol) and dicyclohexano-18-crown-6 (0.074 g, 0.2 mmol) were dissolved in DMF (1 mL) and reacted at 150° C. under nitrogen for 30 minutes. The product was purified in a similar fashion to that of $F_2$—SiPc resulting in a Yield of 0.042 g (42%). UV-vis (DMSO) $\lambda_{max}$=676 nm; HRMS [M+] calculated 600.0747, found 600.0738. The produced molecule has the following structure:

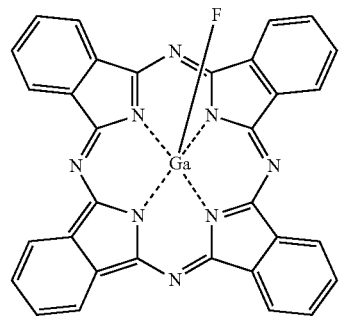

Example 4

Synthesis of Difluorogermaniumphthalocyanine ($F_2$—GePc)

The synthesis of $F_2$—GePc was performed under similar conditions to that of F—GaPc, except using $Cl_2$—GePc as the starting material and using 18-crown-6 instead of dicyclohexano-18-crown-6. UV-vis (DMSO) $\lambda_{max}$=680 nm; HRMS [M+] calculated 624.0678, found 624.0690. The produced molecule has the following structure:

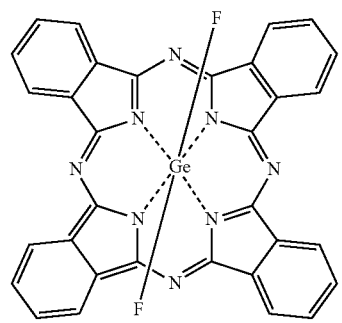

Example 5

Comparison of the Compound of the Present Invention (F—AlPc) to a Comparative Compound Cl—AlPc The compound of the present invention as (F—AlPc, Example 2) was compared to a comparative known compound (Cl—AlPc) using UV-vis spectroscopy, cyclic voltammetry, and thermogravimetric analysis.

Figure 2:
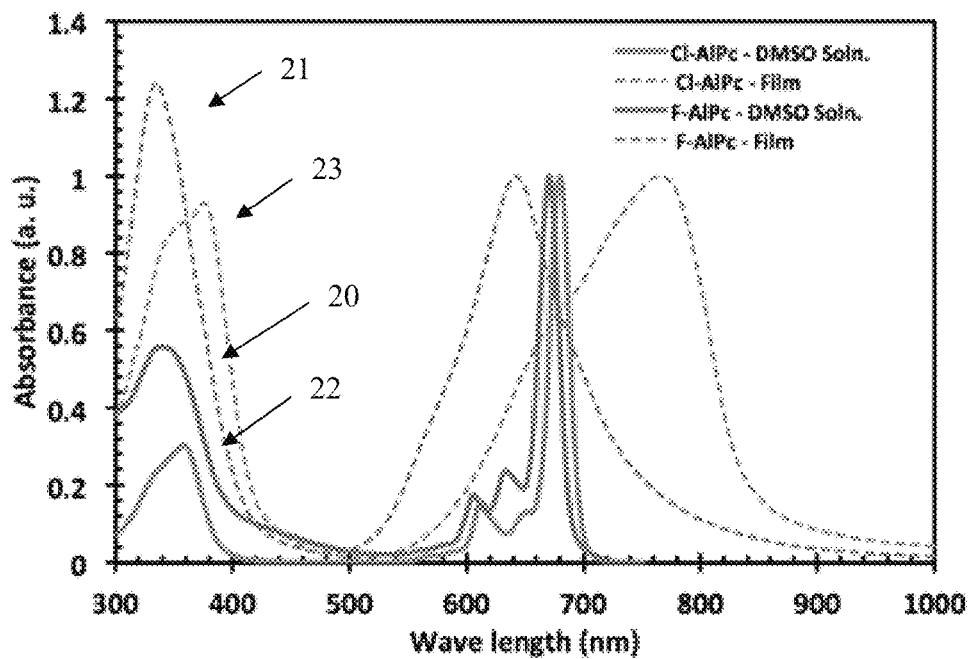
FIG. 2: UV-vis absorbance spectra of F—AlPc and Cl—AlPc as DMSO solutions and as films.

UV-vis spectroscopy. The effect of substitution of the chloride for the fluoride group on the AlPc was characterized first by UV-vis spectroscopy. Both compounds were analyzed in DMSO, chloroform and toluene solution as well as in 40-50 nm thick solid films that were produced by thermal sublimation. FIG. 2 is normalized UV-vis absorbance spectra of F—AlPc and Cl—AlPc in a DMSO solution and as a film. FIG. 2 shows the characteristic scaled absorbance of inventive compound F—AlPc and comparative compound Cl—AlPc in DMSO solution and as a solid film. Data (20) represents F—AlPc in DMSO solution, data (21) represents F—AlPc as a film, data (22) represent Cl—AlPc in DMSO solution, and data (23) represent Cl—AlPc as a film. The optical band gap (Eg,opt) and max absorbance (λmax) were determined from the absorbance spectra and can be found in Table 1. The peak absorption of Cl—AlPc, in DMSO, occurs at $\lambda_{max}$=680 nm, while the peak absorption of F—AlPc is slightly hypsochromically shifted to $\lambda_{max}$=671 nm (FIG. 2). This small hypsochromic shift in absorbance corresponds to an increase in optical bang gap from Eg,opt=1.78 eV to Eg,opt=1.81 eV, for Cl—AlPc to F—AlPc respectively (Table 1). The Cl—AlPc film had a bathocromic shift (771 nm) as compared to the absorbance measured in a DMSO solution. The F—AlPc film had a hypsochromic shift (647 nm) as compared to the absorbance of F—AlPc DMSO solution. Without wishing to be bound by theory, it is believed that the rare occurrence of the hypsochromic shift indicated a potential unique solid state organization of the small molecules.

TABLE 1

| Sample | $\lambda_{MAX}$ (DMSO/Film) (nm) | $E_{Opt\ gap}$ (DMSO/Film) (eV) | $\Phi_{XPS}/\Phi_{UPS}$ (eV) | $E_{HOMO,\ UPS}$ (eV) |
| --- | --- | --- | --- | --- |
| Cl-AlPc | 680/771 | 1.78/1.48 | 4.5/4.4 | 5.7 |
| F-AlPc | 671/647 | 1.81/1.61 | 3.6/3.6 | 4.7 |

Cyclic Voltammetry. Inventive product F—AlPc and comparative product Cl—AlPc were both characterized by cyclic voltammetry in dichloromethane solution. The results are summarized in Table 1. Inventive product F—AlPc exhibited a decrease in oxidation peak potential, $E_{OX,\ peak}$=+1.18 V and an increase in reduction peak potential, $E_{Red,\ peak}$=-0.81 V as compared to the comparative product Cl—AlPc ($E_{OX,\ peak}$=+1.40 V and $E_{Red,\ peak}$=-0.71 V). As a comparison to the cyclic voltammetry results, modeling was performed on the inventive and comparative products (F—AlPc and Cl—AlPc) at the semi-empirical level using the PM3 parameter set in order to determine the effect of axial substitution on the energy levels of the highest occupied molecular orbital ($E_{HOMO}$), lowest unoccupied molecular orbital ($E_{LUMO}$) and energy bandgap ($E_{GAP}$). From the modeling it was seen that the substitution of a chlorine group for a fluorine group consistently resulted in a decrease in $E_{HOMO}$, $E_{LOMO}$ and $E_{GAP}$ of as much as 0.1 eV. This decrease in energy levels observed by DFT calculations was less than the difference in oxidation and reduction peaks observed by cyclic voltammetry, which suggested a of solid-state interaction in the F—AlPc product.

Figure 3:
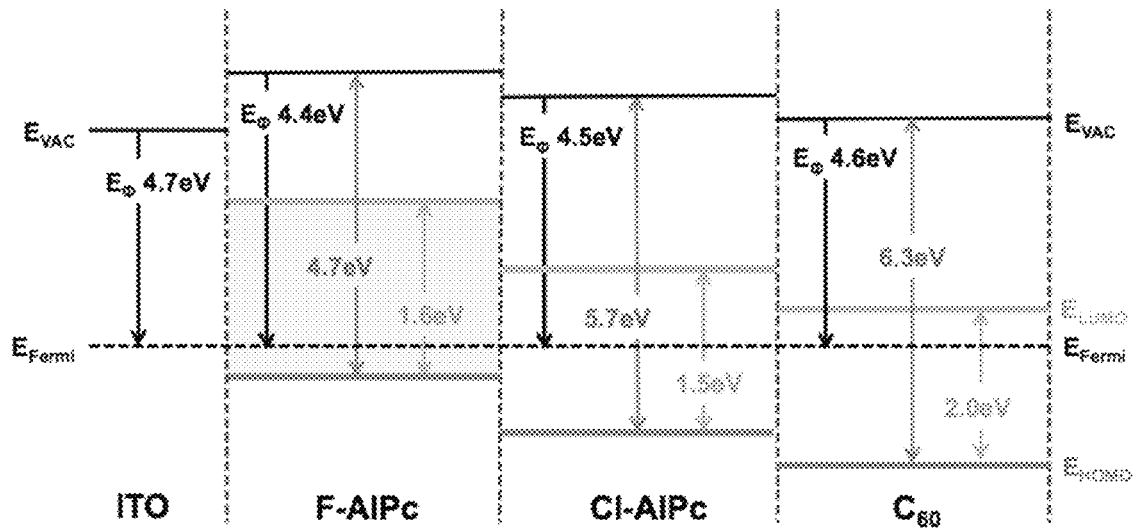
FIG. 3: schematic view of the HOMO levels and local vacuum level shifts for ITO/F—AlPc/Cl—AlPc/$C_{60}$ heterojunctions.

Ultraviolet Photoelectron Spectroscopy Analysis. Ultraviolet photoelectron spectroscopy (UPS) on thin films was also used to determine the $E_{HOMO}$ energy levels of comparative product Cl—AlPc and inventive product F—AlPc. The work functions determined by UPS ($\Phi_{UPS}$) and x-ray photoelectron spectroscopy ($\Phi_{XPS}$) are summarized in Table 1. Details on the UPS characterization can be found in the supporting information. From the data, the substitution of the chloride for a fluoride resulted in a significant change in $\Phi_{UPS}$, $\Phi_{XPS}$ and ultimately $E_{HOMO}$. For example, an increase in $E_{HOMO}$ of as much as ≈1.0 eV was observed between comparative product Cl—AlPc ($E_{HOMO}$=-5.7 eV) and inventive product F—AlPc ($E_{HOMO}$=-4.7 eV). Similarly to electrochemistry, the magnitude of the experimentally obtained $E_{HOMO}$ increase was considered significant as compared to the DFT calculations. The $\Phi_{UPS}≈\Phi_{XPS}$ confirmed the obtained calculated values. FIG. 3 is a schematic view of the HOMO levels and local vacuum level shifts for ITO/F—AlPc/Cl—AlPc/$C_{60}$ heterojunctions. For comparison the Fermi energy levels were all assumed to be equal. The HOMO levels were obtained by UPS and the LUMO energy levels for Cl—AlPc and F—AlPc were estimated from the onset of the solid state UV-Vis absorbance (FIG. 2). FIG. 3 illustrates the $E_{HOMO}$ calculated by UPS and the $E_{LUMO}$ levels estimated from the difference between $E_{HOMO}$ and $E_{Opt\ gap}$ (determined by absorption data of the film) for F—AlPc and Cl—AlPc in addition to the literature values for Fullerene ($C_{60}$).

Thermo Gravimetric Analysis. Thermo gravimetric analysis (TGA) was performed on both comparative product Cl—AlPc and inventive product F—AlPc to study the mass loss with respect to the change in temperature. F—AlPc appeared not to exhibit mass loss until roughly 625° C. (ambient pressure) while Cl—AlPc began to experience significant mass loss at 550° C. (ambient pressure). These results further suggest significant solid-state interaction for the F—AlPc compared to Cl—AlPc resulting in a higher thermal stability.

Example 6

Comparative Device A and Characterization

A comparative PHJ OPV device (device A) with a device architecture of ITO/PEDOT:PSS/Cl—AlPc(20 nm)/$C_{60}$(40 nm)/BCP(7.5 nm)/Ag(80 nm) was fabricated and characterized having a short-circuit current density ($J_{SC}$) of 3.85 mA/cm$^2$, an open voltage circuit ($V_{OC}$) of 0.67 V, a fill factor (FF) of 0.48 and efficiency (η) of 1.23%. The electrical characteristics for this comparative Cl—AlPc/$C_{60}$ OPV device are summarized in Table 2.

Example 7

Devices B-D Containing F—AlPc

Devices B through D were fabricated with a similar architecture to device A. Device B contained F—AlPc (ITO/PEDOT:PSS:PSS/F—AlPc(20 nm)/$C_{60}$(40 nm)/BCP(8 nm)/Ag(80 nm)). Device C contained an equal amount of F—AlPc and Cl—AlPc films (ITO/PEDOT:PSS:PSS F—AlPc(10 nm)/Cl—AlPc(10 nm)/$C_{60}$(40 nm)/BCP(8 nm)/Ag(80 nm)). Device D had a 2:1 ratio of F—AlPc and Cl—AlPc films. (ITO/PEDOT:PSS:PSS F—AlPc(20 nm)/Cl—AlPc(10 nm)/$C_{60}$(40 nm)/BCP(8 nm)/Ag(80 nm)). The electrical characteristics of the devices are summarized Table 2.

TABLE 2

| Device[a] | Active layer (nm) | $V_{OC}$[b] (V) | $J_{SC}$[b] (mA·cm$^{-2}$) | FF[b] | $\eta_{Power}$[b] (%) |
|---|---|---|---|---|---|
| A | Cl-AlPc (20 nm)/C$_{60}$ (40 nm) | 0.67 ± 0.03 | −3.85 ± 0.3 | 0.48 ± 0.03 | 1.23 ± 0.17 |
| B | F-AlPc (20 nm)/C$_{60}$ (40nm) | 0.27 ± 0.02 | −0.7 ± 0.07 | 0.24 ± 0.02 | 0.05 ± 0.006 |
| C | F-AlPc (10 nm)/Cl-AlPc (10 nm)/C$_{60}$ (40nm) | 0.45 ± 0.01 | −4. ± 0.5 | 0.34 ± 0.03 | 0.61 ± 0.1 |
| D | F-AlPc (20 nm)/Cl-AlPc (40 nm) | 0.37 ± 0.008 | −1.23 ± 0.2 | 0.28 ± 0.01 | 0.12 ± 0.02 |

[a]Device structure: ITO/Pedot:PSS/(Active layer)/BCP(7.5 nm)/Ag(80 nm).
[b]Devices characteristics taken from an average of 6-10 pixels over 2-4 devices.

Example 8

Comparison of Devices B-D Containing F—AlPc to Comparative Device A

Figure 4:
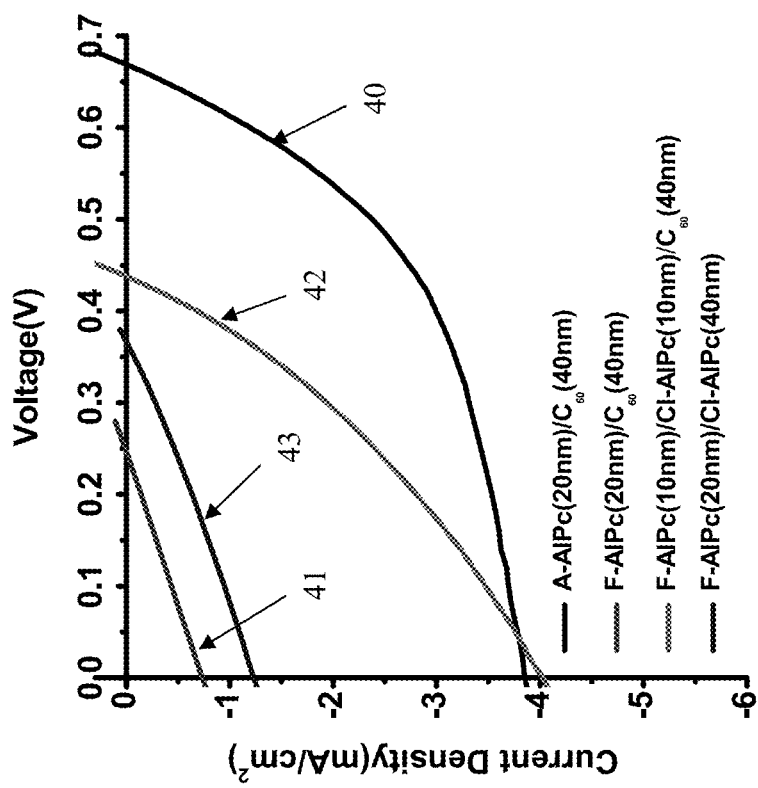
FIG. 4: J-V curves for the series of F—AlPc/Cl—AlPc and C60 containing OPT devices.
Figure 5:
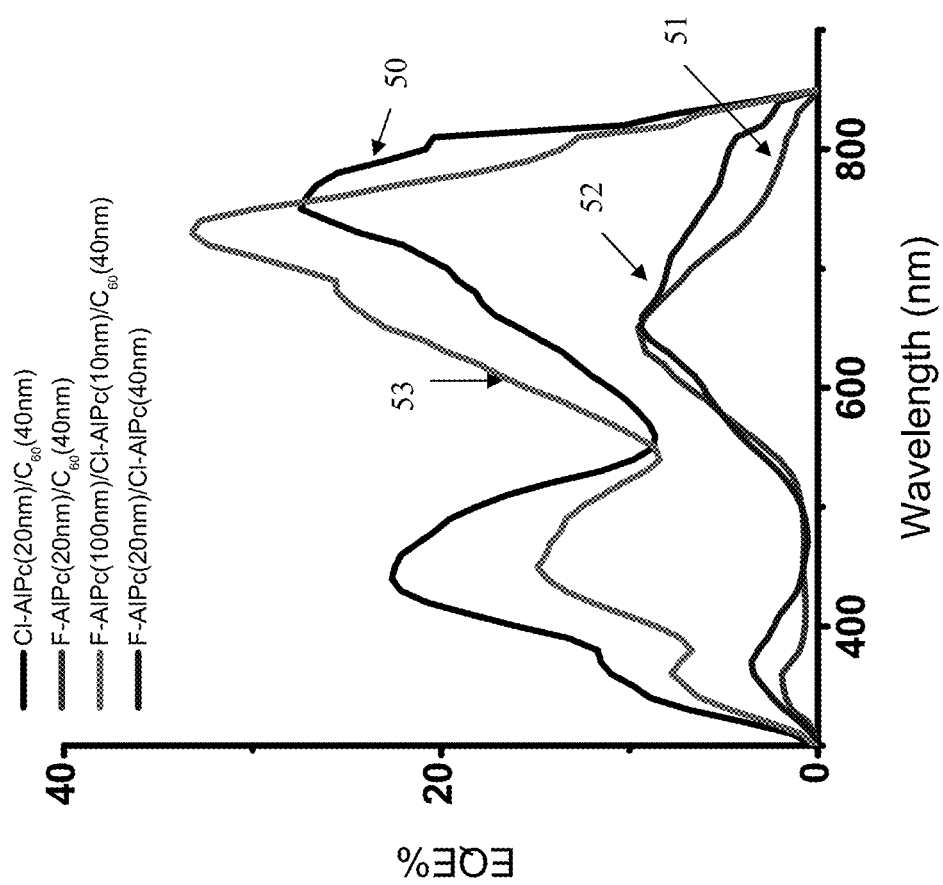
FIG. 5 Plots of external quantum efficiency for the series of F—AlPc/Cl—AlPc and C60 containing OPT devices.

The inventive devices B-D and comparative device were compared using J-V curves, external quantum efficiency. The J-V curves and external quantum efficiency for the series of F—AlPc/Cl—AlPc and C$_{60}$ containing OPV devices were plotted. FIG. 4 are J-V curves for the series of F—AlPc/Cl—AlPc and C$_{60}$ containing OPV devices. Data (40) represents comparative compound Cl—AlPc (20 nm) and C$_{60}$ (40 nm) containing device, data (41) represents F—AlPc (20 nm) and C$_{60}$ (40 nm) containing device, data (42) presents F—AlPc (10 nm), Cl—AlPc (10 nm) and C$_{60}$ (40 nm) containing device and data (43) represents F—AlPc (20 nm) and Cl—AlPc (40 nm) containing device. FIG. 5 plots of are external quantum efficiency (EQE) for the series of F—AlPc/Cl—AlPc and C$_{60}$ containing OPV devices. Data (50) represents comparative compound Cl—AlPc (20 nm) and C$_{60}$ (40 nm) containing device, data (51) represents F—AlPc (20 nm) and C$_{60}$ (40 nm) containing device, data (52) presents F—AlPc (10 nm), Cl—AlPc (10 nm) and C$_{60}$ (40 nm) containing device and data (53) represents F—AlPc (20 nm) and Cl—AlPc (40 nm) containing device. From the data in Table 2, it can be concluded that Device B (F—AlPc) had a significant drop in $V_{OC}$, $J_{SC}$ and FF as compared to Comparative Device A. The EQE plots (FIG. 5) demonstrated a contribution to photo-generation at 620 nm, which corresponded to the absorption of F—AlPc (FIG. 2). Devices C and D when compared to comparative Device A had a decrease in VOC of 0.22 V, but an increase in JSC of 0.15 mA·cm-2 (FIGS. 4 and 5, Table 2). The EQE spectra for device C indicated a greater ratio of the AlPc peaks (600-800 nm) to C$_{60}$ peaks (350-500 nm) as compared to comparative device A, which did not have any F—AlPc, which indicated a more significant photo-generation when utilizing both Cl—AlPc and F—AlPc as compared to just one or the other (FIG. 3). Without wishing to be bound by theory, it is believed that the drop in $V_{OC}$, $J_{SC}$ and FF is due to the relatively high $E_{HOMO}$ level of F—AlPc compared to Cl—AlPc (Table 1, Table 2 & FIGS. 4 and 5). It is further believed that the maximum $V_{oc}$ depends on the energy difference between the highest occupied molecular orbital (HOMO) of the donor the lowest unoccupied molecular orbital (LUMO) of the acceptor at the interface in a PHJ device, which is also referred to as the interface gap ($I_g$). As seen in FIG. 3, $I_g$ for Cl—AlPc/C$_{60}$ is 1.4 V and for F—AlPc/C$_{60}$ was 0.4 V, indicating that this reduction in $I_g$ could be one of the main factors responsible for the reduction in $V_{OC}$ (Table 2). Further analysis of the respective HOMO and LUMO energies of F—AlPc and Cl—AlPc (FIG. 3) indicates that the two could be paired within an OPV as an electron donor and electron acceptor respectively.

The electrical properties of Device D demonstrated that Cl—AlPc can be used as an electron acceptor in PHJ-OPVs.

In sum, from the data in Example 7, devices (B-D) of the present invention having a photoactive layer including an axially fluorinated metal phthalocyanines can be used as photovoltaic cell.

The invention claimed is:

1. A method of making an axially fluorinated metal phthalocyanine, the method comprising:
   (a) obtaining a composition comprising an aprotic fluoride compound, a solvent, and a compound having the following structure:

$X_m Y_n$-MPc; and (b) heating the composition for a sufficient period of time to produce an axially fluorinated metal phthalocyanine having the following structure:

$F_m Y_n$-MPc, where
   X and Y are each individually Cl, Br, I, or —OH,
   m is 1 or 2,
   n is 0 or 1,
   M is a trivalent or tetravalent metal, and
   Pc is a phthalocyanine,
   wherein the aprotic fluoride compound has the following structure:

$Z(F)_o$, wherein Z is a group I or II metal, a tetra alkylated ammonium ion, or a tetra alkylated phosphonium ion, and o is 1 or 2.

2. The method of claim 1, wherein Z is a group I metal selected from Cs, Rb, K, Na, or Li, or more preferably Cs, Rb, or K.

3. The method of claim 1, wherein Z is a group II metal selected from Ba, Sr, Ca, Mg, or Be, or more preferably Ba, Sr, or Ca.

4. The method of claim 1, wherein X is Cl, m is 1 or 2, and n is 0.

5. The method of claim 1, wherein m is 1 and n is 1.

6. The method of claim 1, wherein M is a Group III metal selected from the group consisting of Al, Ga, or In.

7. The method of claim 1, wherein M is a Group IV metal selected from the group consisting of Si, Ge, or Sn.

8. The method of claim 1, wherein the produced axially fluorinated metal phthalocyanine has the following structure:

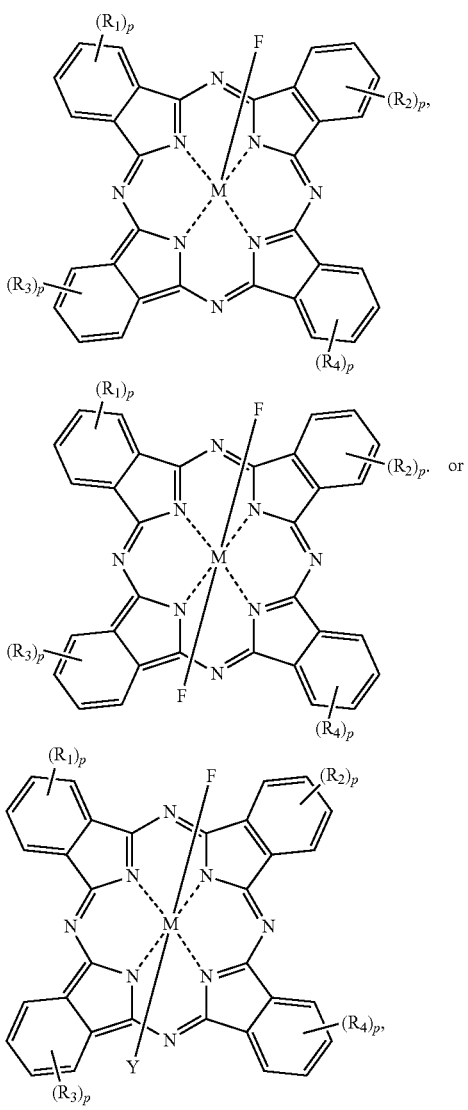

where
R$_1$, R$_2$, R$_3$, and R$_4$ are each individually a hydrogen, a hydrocarbon, or a halogen, and
p is an integer from 0 and 4.

9. The method of claim 8, wherein R$_1$ to R$_4$ are each individually a substituted or un-substituted hydrocarbon.

10. The method of claim 9, wherein the hydrocarbon is a methyl, ethyl, propyl, isopropyl, n-butyl, sec-butyl or tert-butyl group.

11. The method of claim 8, wherein R$_1$ to R$_4$ are each individually a halogen selected from F, Cl, Br, or I.

12. The method of claim 1, wherein the composition further comprises a chelating agent.

13. The method of claim 12, wherein the chelating agent is a glycol, glycol mono ether, glycol bis ether, polyethylene glycol, polyethylene glycol mono ether, polyethylene glycol bis ether or a crown ether.

14. The method of claim 13, wherein the crown ether is 18-crown-6 or dicyclohexyl-18-crown-6, dibenzo-18-crown-6, 15-crown-5, 12-crown-4, benzo-15-crown-5, benzo-18-crown-6, 4-aminobenzo-18-crown-6, 4'-nitrobenzo-15-crown-5 or the like.

15. The method of claim 1, wherein the aprotic fluoride compound and the compound having the structure X$_m$Y$_n$-MPc are each partially or fully solubilized in the composition.

16. The method of claim 15, wherein the chelating agent is partially or fully solubilized in the composition.

17. The method of claim 1, wherein the solvent is an aprotic solvent.

18. The method of any one of claim 1, wherein the composition is heated to a temperature of 30 to 250° C. for 1 to 600 minutes.

19. The method of claim 1, wherein the composition in step (a) comprises 0.5 to 45% wt. of aprotic fluoride compound, and 0.1 to 50% wt. of the compound having the structure X$_m$Y$_n$-MPc.

20. The method of claim 1, further comprising purifying or isolating the produced compound.

21. The method of claim 1, wherein the composition in step (a) does not include a protic compound or does not include a protic fluoride compound or does not include an acid.

22. The method of claim 21, wherein the protic fluoride compound is hydrogen fluoride.

23. The method of claim 1, wherein the method does not produce hydrogen fluoride or hydrofluoric acid as a by-product or produces only trace amounts of said hydrogen fluoride or hydrochloric acid.

24. A process for making a photoactive layer on a substrate, wherein the photoactive layer comprises an axially fluorinated metal phthalocyanine, the process comprising depositing the axially fluorinated metal phthalocyanine on at least a portion of a surface of the substrate, wherein the axially fluorinated metal phthalocyanine is obtained by:
(a) obtaining a composition comprising an aprotic fluoride compound, a solvent, and a compound having the following structure:

X$_m$Y$_n$-MPc; and (b) heating the composition for a sufficient period of time to produce an axially fluorinated metal phthalocyanine having the following structure:

F$_m$Y$_n$-MPc, where
X and Y are each individually Cl, Br, I, or —OH,
m is 1 or 2,
n is 0 or 1,
M is a trivalent or tetravalent metal, and
Pc is a phthalocyanine,
wherein the aprotic fluoride compound has the following structure:

Z(F)$_o$, wherein Z is a group I or II metal, a tetra alkylated ammonium ion, or a tetra alkylated phosphonium ion, and o is 1 or 2.

25. A composition comprising:
(a) an aprotic fluoride compound, wherein the aprotic fluoride compound has the following structure:

Z(F)$_o$, wherein Z is a group I or II metal, a tetra alkylated ammonium ion, or a tetra alkylated phosphonium ion, and o is 1 or 2;
(b) a solvent; and
(c) a compound having the following structure:

X$_m$Y$_n$-MPc; and where
X and Y are each individually Cl, Br, I, or —OH,
m is 1 or 2,
n is 0 or 1,
M is a trivalent or tetravalent metal, and
Pc is a phthalocyanine.

* * * * *